United States Patent
Shigaki et al.

(10) Patent No.: US 8,513,520 B2
(45) Date of Patent: Aug. 20, 2013

(54) DYE-SENSITIZED PHOTOVOLTAIC DEVICE COMPRISING A RUTHENIUM METAL COMPLEX

(75) Inventors: Koichiro Shigaki, Tokyo (JP); Masayoshi Kaneko, Tokyo (JP); Teruhisa Inoue, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 179 days.

(21) Appl. No.: 13/058,407

(22) PCT Filed: Aug. 21, 2009

(86) PCT No.: PCT/JP2009/064656
§ 371 (c)(1), (2), (4) Date: Feb. 10, 2011

(87) PCT Pub. No.: WO2010/021378
PCT Pub. Date: Feb. 25, 2010

(65) Prior Publication Data
US 2011/0132452 A1  Jun. 9, 2011

(30) Foreign Application Priority Data

Aug. 22, 2008  (JP) .................................. 2008-214001

(51) Int. Cl.
*H01L 31/00* (2006.01)
*C07F 15/00* (2006.01)

(52) U.S. Cl.
USPC ............................................. 136/263; 546/2

(58) Field of Classification Search
USPC ............ 136/263; 544/225; 546/2; 556/137
See application file for complete search history.

(56) References Cited

U.S. PATENT DOCUMENTS

| | | | |
|---|---|---|---|
| 4,927,721 A | 5/1990 | Gratzel et al. | |
| 7,126,013 B2 * | 10/2006 | Heeney et al. | 549/59 |
| 7,141,735 B2 | 11/2006 | Ikeda et al. | |
| 7,321,037 B2 | 1/2008 | Wu et al. | |
| 7,538,217 B1 | 5/2009 | Lin et al. | |
| 2003/0152827 A1 | 8/2003 | Ikeda et al. | |
| 2007/0265443 A1 | 11/2007 | Wu et al. | |
| 2008/0110497 A1 * | 5/2008 | Inoue et al. | 136/256 |

FOREIGN PATENT DOCUMENTS

| | | |
|---|---|---|
| JP | 2664194 B | 10/1997 |
| JP | 2007-302879 A | 11/2007 |
| JP | 2008-21496 A | 1/2008 |
| JP | 2009-179629 A | 8/2009 |
| WO | 02/011213 A1 | 2/2002 |
| WO | 2009/020098 A1 | 2/2009 |

OTHER PUBLICATIONS

Mohanakrishnan et al., "Synthesis and characterization of 9,9-dialkylfluorene capped benzo[c]thiophene/benzo[c]selenophene analogs as potential OLEDs", Tetrahedron Letters 49, p. 4792-4795 (2008). Available online May 28, 2008.*
Chen et al., "A ruthenium complex with superhigh light-harvesting capacity for dye-sensitized solar cells," Angewandte Chemie Intl. Edition 45, p. 5822-5825 (2006).*
Nature, vol. 353, Oct. 24, 1991, pp. 737-739, "A low-cost, high-efficiency solar cell based on dye-sensitized colloidal RiO2 films", O'Regan, et al.
J. Am. Chem. Soc., V. 115, 1993, pp. 6382-6390, "Conversion of Light to Electricity by cis-X2Bis(2,2'-bipyridyl-4,4'-dicarboxylate)ruthenium(II)Charge-Transfer Sensitizers (X=Cl-, Br-, I-, Cn-, and SCN-) on Nanocrystalline TiO2 Electrodes", Nazeeruddin, et al.
Chemistry Letters, 1998, pp. 1241-1242, "Fabrication of Quasi-solid-state Dye-sensitized TiO2 Solar Cells Using Low Molecular Weight Gelators", Kubo, et al.
Synthesis No. 17, (2007), pp. 2711-2719, "Synthesis of Amino-Functionalized 2,2'-Bipyridines", Hapke et al.
International Search Report dated Nov. 24, 2009 in corresponding foreign application No. PCT/JP2009/064656.
European Communication dated Sep. 2, 2011 in corresponding foreign patent application No. EP 09808314.0, 4 pages.
J. Am. Chem. Soc., 2006, V 128 No. 51, pp. 16701-16707, "Molecular Engineering of Organic Sensitizers for Solar Cell Applications", XP-002650103, Kim, et al.

* cited by examiner

*Primary Examiner* — Jeffrey T Barton
*Assistant Examiner* — Eric R Smith
(74) *Attorney, Agent, or Firm* — Nields, Lemack & Frame, LLC

(57) ABSTRACT

Disclosed is a dye-sensitized photovoltaic device in which a metal complex dye represented by Formula (1), or a salt thereof, is carried on a thin film of oxide semiconductor micrograins disposed on a substrate. (In Formula (1), $m_1$ represents an integer from 1 to 2 and $n_1$ represents an integer from 1 to 3. $X_1$ represents an oxygen atom or sulfur atom. $Y_1$ and $Y_2$ each independently represent a thiocyanate group (—SCN) or isothiocyanate group (—NCS). $M_1$ and $M_2$ represent hydrogen atoms. $R_1$ and $R_2$ represent hydrogen atoms. $R_3$ and $R_4$ each independently represent a straight-chain alkyl group with 1 to 6 carbons. Further, when $m_1$ is 2 and there are multiple of each of $R_3$ and $R_4$, each of $R_3$ and $R_4$ may be the same as or different from one another.)

14 Claims, No Drawings

DYE-SENSITIZED PHOTOVOLTAIC DEVICE COMPRISING A RUTHENIUM METAL COMPLEX

TECHNICAL FIELD

The present invention relates to a photoelectric conversion device having a thin film of semiconductor fine particles sensitized with a metal complex dye or a salt thereof, and a solar cell using the same, and more specifically, a photoelectric conversion device in which a metal complex compound (metal complex dye) having a specific structure is carried on a thin film of oxide semiconductor fine particles and a solar cell utilizing the same.

BACKGROUND ART

A solar cell utilizing sunlight draws attention as an energy resource replacing fossil fuel such as petroleum and coal. At present, a silicon solar cell using crystalline or amorphous silicon, a compound semiconductor solar cell using gallium, arsenic etc. and the like are actively developed and studied. However, they have a problem that they are difficult to be used widely due to a high energy and cost required for the production thereof. A photoelectric conversion device using a semiconductor fine particle sensitized with a dye, or a solar cell using the same is also known, and a material and production technique for producing the same are disclosed (see Patent Document 1, Non Patent Document 1, Non Patent Document 2). This photoelectric conversion device is produced by use of a relatively inexpensive oxide semiconductor such as titanium oxide. Therefore, this photoelectric conversion device draws attention by the reasons that there is a possibility to obtain a photoelectric conversion device of a lower cost compared with a conventional solar cell using silicon etc., and that a colorful solar cell can be obtained, and the like. However, there remains a problem of the conversion efficiency lower than a silicon solar cell, and then further improvement of the conversion efficiency is desired (see Patent Document 1).

PRIOR ART DOCUMENT

Patent Document

Patent Document 1: Japanese Patent No. 2664194
Patent Document 2: WO 2002/011213

Non Patent Document

Non Patent Document 1: B. O'Regan et al. Nature, Vol. 353, page 737 (1991)
Non Patent Document 2: M. K. Nazeeruddin et al. J. Am. Chem. Soc., Vol. 115, page 6382 (1993)
Non Patent Document 3: W. Kubo et al. Chem. Lett., page 1241 (1998)
Non Patent Document 4: Marko Hapke et al. Synthesis No. 17, pages 2711 to 2719 (2007)

SUMMARY OF INVENTION

Problem to be Solved by the Invention

In a photoelectric conversion device using an oxide semiconductor fine particle sensitized with a metal complex dye, a stable photoelectric conversion device having a high conversion efficiency and high usefulness is needed to be developed.

Means for Solving the Problem

The present inventors made a dedicated effort to solve the above problem, and as a result, have found that the above problem can be solved by sensitizing a thin film of semiconductor fine particles using a methine dye having a specific structure, and producing a photoelectric conversion device, and have completed the present invention.

That is to say, the present invention is:
(1) a photoelectric conversion device in which a metal complex dye represented by following Formula (1) or a salt thereof is carried on a thin film of oxide semiconductor fine particles disposed on a substrate:

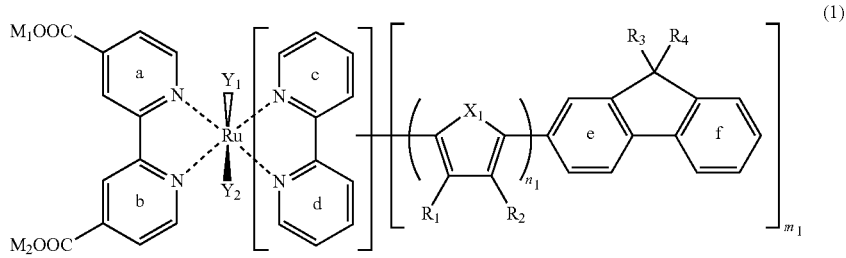

(1)

wherein, $m_1$ represents an integer of 1 to 2, $n_1$ represents an integer of 1 to 3; $X_1$ represents an oxygen atom or a sulfur atom; $Y_1$ and $Y_2$ each independently represent a thiocyanate group (—SCN) or an isothiocyanate group (—NCS); $M_1$ and $M_2$ represent a hydrogen atom; $R_1$ and $R_2$ represent a hydrogen atom; $R_3$ and $R_4$ each independently represent a straight alkyl group of 1 to 6 carbon atoms; with the proviso that when $m_1$ is 2 and R3 and R4 each exist in a plural number, then each $R_3$ and $R_4$ may be the same or different from each other;
(2) the photoelectric conversion device described in (1), wherein $X_1$ in Formula (1) is a sulfur atom;
(3) the photoelectric conversion device described in (2), wherein $n_1$ in Formula (1) is 1;
(4) the photoelectric conversion device described in (3), wherein $Y_1$ and $Y_2$ in Formula (1) are each an isothiocyanate group (—NCS);
(5) the photoelectric conversion device described in (4), wherein $R_3$ and $R_4$ in Formula (1) are each independently a straight alkyl group of 3 to 5 carbon atoms;
(6) the photoelectric conversion device described in (5), wherein $R_3$ and $R_4$ in Formula (1) are each an n-butyl group;
(7) the photoelectric conversion device described in (6), wherein mi in Formula (1) is 2;
(8) the photoelectric conversion device described in (6), wherein $m_1$ in Formula (1) is 1;

(9) a photoelectric conversion device in which one or more of metal complex dyes represented by Formula (1) described in (1) or a salt thereof, and a methine dye and/or a metal complex dye having a structure other than the Formula (1) are carried on a thin film of oxide semiconductor fine particles disposed on a substrate;
(10) the photoelectric conversion device described in any one of (1) to (9), wherein the thin film contains titanium dioxide, zinc oxide or tin oxide;
(11) the photoelectric conversion device described in any one of (1) to (10), wherein a metal complex dye or a salt thereof is carried under the presence of a chlathrate compound;
(12) a solar cell using a photoelectric conversion device described in any one of (1) to (11);
(13) a metal complex dye represented by Formula (1) described in (1) or a salt thereof; and
(14) a photoelectric conversion device in which a metal complex dye represented by following Formula (1) or a salt thereof is carried on a thin film of oxide semiconductor fine particles disposed on a substrate:

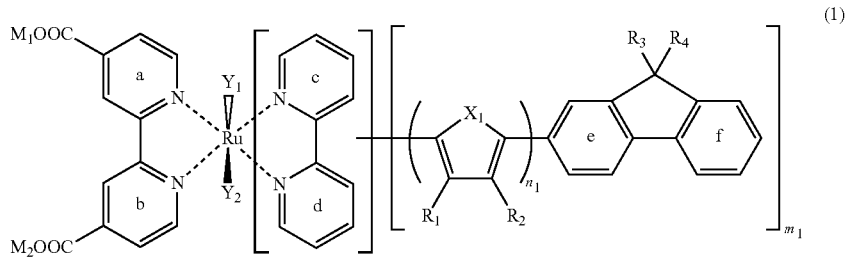

wherein, $m_1$ represents an integer of 1 to 2, $n_1$ represents an integer of 1 to 3; $X_1$ represents an oxygen atom, a sulfur atom, a selenium atom or $=NR_5$ wherein $R_5$ represents a hydrogen atom or an aliphatic hydrocarbon residue which may have a substituent; $Y_1$ and $Y_2$ each independently represent a thiocyanate group (—SCN), a halogen atom or an isothiocyanate group (—NCS); and $Y_1$ and $Y_2$ may be combined together to form one ligand; $M_1$ and $M_2$ each independently represent a hydrogen atom or an ammonium ion; $R_1$ and $R_2$ each independently represent a hydrogen atom, an aliphatic hydrocarbon residue which may have a substituent or an alkoxyl group which may have a substituent; and when $n_1$ is 2 or more, or $m_1$ is 2 and $R_1$ and $R_2$ each exist in a plural number, then each $R_1$ and $R_2$ may be the same or different from each other; and a plural of $R_1$ and/or $R_2$ may form a ring, and further may have a substituent on this ring; $R_3$ and $R_4$ each independently represent a hydrogen atom, an aliphatic hydrocarbon residue which may have a substituent or an aromatic hydrocarbon residue which may have a substituent; when $m_1$ is 2 and $R_3$ and $R_4$ each exist in a plural number, then each $R_3$ and $R_4$ may be the same or different from each other; and $R_3$ and $R_4$ may be combined each other to form a ring which may have a substituent; an aromatic ring a, an aromatic ring b, an aromatic ring c, an aromatic ring d and an aromatic ring e each may have 1 to 3 substituents; and an aromatic ring f may have 1 to 4 substituents.

Advantages of the Invention

A photoelectric conversion device having a high conversion efficiency and high stability and a solar cell can be provided by using a metal complex dye or a salt thereof of the present invention having a specific structure. The metal complex dye of the present invention or a salt thereof has a characteristic of being able to obtain a sufficient conversion efficiency even if a film of oxide semiconductor fine particles on which the dye to be carried is thin.

MODE FOR CARRYING OUT THE INVENTION

The present invention will be described in detail below.

A photoelectric conversion device of the present invention is the photoelectric conversion device in which a metal complex dye represented by following Formula (1) (including a salt thereof hereinafter the same) is carried on a thin film of oxide semiconductor fine particles disposed on a substrate. In the present specification, a "compound" represents, unless otherwise stated, a compound or a salt thereof.

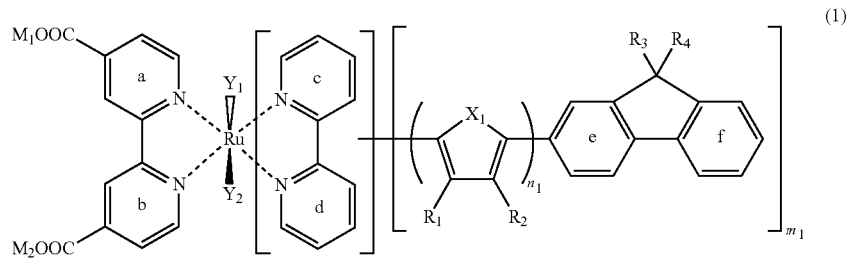

In Formula (1), $m_1$ represents an integer of 1 to 2, $n_1$ represents an integer of 1 to 3, preferably 1.

In Formula (1), $X_1$ represents an oxygen atom, a sulfur atom, a selenium atom or $=NR_5$, preferably an oxygen atom, a sulfur atom or a selenium atom, more preferably an oxygen atom or a sulfur atom, particularly preferably a sulfur atom. Here, $R_5$ represents a hydrogen atom or an aliphatic hydrocarbon residue which may have a substituent.

Examples of the "aliphatic hydrocarbon residue" in the above include a saturated or unsaturated straight, branched or cyclic alkyl group which may have a substituent. Examples of the preferable aliphatic hydrocarbon residue include a saturated or unsaturated straight or branched alkyl group of 1 to 36 carbon atoms which may have a substituent, and examples of the more preferable aliphatic hydrocarbon residue include a saturated or unsaturated straight or branched alkyl group of 1 to 18 carbon atoms which may have a substituent. Examples of the cyclic alkyl group which may have a substituent include a cycloalkyl of 3 to 8 carbon atoms. Specific examples of them include a methyl group, an ethyl group, an n-propyl group, an isopropyl group, an n-butyl group, an iso-butyl group, a t-butyl group, an octyl group, an octadecyl group, an isopropyl group, a cyclohexyl group, a vinyl group, a propenyl group, a pentynyl group, a butenyl group, a hexenyl group, a hexadienyl group, an isopropenyl group, an isohexenyl group, a cyclohexenyl group, a cyclopentadienyl group, an ethynyl group, a propynyl group, a pentynyl group, a hexynyl group, an isohexynyl group and a cyclohexynyl group, respectively. They may have a substituent as described above.

Examples of the substituent include an aromatic residue which may have a substituent, an aliphatic hydrocarbon residue which may have a substituent, a hydroxyl group, a phosphate group, a cyano group, a nitro group, a halogen atom, a carboxyl group, a carbonamide group, an alkoxycarbonyl group, an arylcarbonyl group, an alkoxyl group, an aryloxy group, a substituted amide group, an acyl group and a substituted or unsubstituted amino group.

The "aromatic residue" in the above means a group which is obtained by removing one hydrogen atom from an aromatic ring. Specific examples of the aromatic ring include an aromatic hydrocarbon ring such as benzene, naphthalene, anthracene, phenanthrene, pyrene, perylene and terylene; a heteroaromatic ring such as indene, azulene, pyridine, pyrazine, pyrimidine, pyrazole, pyrazolidine, thiazolidine, oxazolidine, pyran, chromene, pyrrole, pyrrolidine, benzimidazole, imidazoline, imidazolidine, imidazole, pyrazole, triazole, triazine, diazole, indoline, thiophene, thienothiophene, furan, oxazole, oxadiazole, thiazin, thiazole, indole, benzothiazole, benzothiadiazole, naphthothiazole, benzoxazole, naphthoxazole, indolenine, benzoindolenine, pyrazine, quinoline and quinazoline; and a condensed aromatic ring such as fluorene and carbazole. Preferred is an aromatic residue having an aromatic ring (a fused ring including an aromatic ring and an aromatic ring) of 5 to 16 carbon atoms.

The "aliphatic hydrocarbon residue" in the above may be the same as those stated in the section of $X_1$.

Examples of the "halogen atom" in the above include a fluorine atom, a chlorine atom, bromine and an iodine atom. The "halogen atom" is preferably a fluorine atom or a chlorine atom, further preferably a chlorine atom.

Examples of the "alkoxycarbonyl group" in the above include an alkoxycarbonyl group of 1 to 10 carbon atoms. Specific examples of the "alkoxycarbonyl group" include a methoxycarbonyl group, an ethoxycarbonyl group, an n-propoxycarbonyl group, an isopropoxycarbonyl group, an n-butoxycarbonyl group, an isobutoxycarbonyl group, a sec-butoxycarbonyl group, a t-butoxycarbonyl group, an n-pentoxycarbonyl group, an n-hexyloxycarbonyl group, an n-heptyloxycarbonyl group, an n-nonyloxycarbonyl group and an n-decyloxycarbonyl group.

Examples of the "arylcarbonyl group" in the above include a group in which an aryl group such as benzophenone and naphthophenone and carbonyl are linked together.

Examples of the alkoxyl group include a methoxy group, an ethoxy group, an n-propoxy group, an isopropoxy group, an n-butoxy group, an isobutoxy group, a sec-butoxy group and a tert-butoxy group. They may further have a substituent.

Examples of the "aryloxy group" in the above preferably include a phenoxy group and a naphthoxy group, which may have a phenyl group and a methyl group as a substituent.

Specific examples of the "substituted amide group" in the above include an amide group such as an amide group, an acetoamide group, an N-methylamide group, an N-ethylamide group, an N-(n-propyl)amide group, an N-(n-butyl)amide group, an N-isobutylamide group, an N-(sec-butylamide) group, an N-(t-butyl)amide group, an N,N-dimethylamide group, an N,N-diethylamide group, an N,N-di(n-propyl)amide group, an N,N-di(n-butyl)amide group, an N,N-diisobutylamide group, an N-methylacetoamide group, an N-ethylacetoamide group, an N-(n-propyl)acetoamide group, an N-(n-butyl)acetoamide group, an N-isobutylacetoamide group, an N-(sec-butyl)acetoamide group, an N-(t-butyl)acetoamide group, an N,N-dimethylacetoamide group, an N,N-diethylacetoamide group, an N,N-di(n-propyl)acetoamide group, an N,N-di(n-butyl)acetoamide group and an N,N-diisobutylacetoamide group; an acetoamide group and an alkyl amide group; or an arylamide group such as a phenylamide group, a naphthylamide group, a phenylacetoamide group and a naphthylacetoamide group.

Examples of the "acyl group" in the above include an alkylcarbonyl group of 1 to 10 carbon atoms and an arylcarbonyl group. The "acyl group" is preferably an alkylcarbonyl group of 1 to 4 carbon atoms, and specific examples of the "acyl group" include an acetyl group, a propionyl group, a trifluoromethylcarbonyl group, a pentafluoroethylcarbonyl group, a benzoyl group and a naphthoyl group.

Examples of the "substituted or unsubstituted amino group" in the above include an amino group; an alkyl-substituted amino group such as a mono- or dimethylamino group, a mono- or diethylamino group, a mono- or di(n-propyl)amino group, a mono- or di(n-butyl)amino group and a mono- or di(n-hexyl)amino group; an aromatic-substituted amino group such as a mono- or diphenylamino group and a mono- or dinaphthylamino group; an amino group or benzylamino group substituted with one alkyl group and one aromatic hydrocarbon residue such as a monoalkylmonophenylamino group; and an acetylamino group and a phenylacetylamino group.

In Formula (1), $Y_1$ and $Y_2$ each independently represent a thiocyanate group (—SCN), a halogen atom or an isothiocyanate group (—NCS), preferably a thiocyanate group (—SCN) or an isothiocyanate group (—NCS), more preferably an isothiocyanate group (—NCS). Furthermore, $Y_1$ and $Y_2$ may be combined together to form one ligand. The "halogen atom" may be the same as those stated in the section of $X_1$.

In Formula (1), $M_1$ and $M_2$ each independently represent a hydrogen atom or ammonium ion, preferably a hydrogen atom. Examples of the ammonium ion include an alkylammonium ion such as a tetramethylammonium ion, a tetrabutylammonium ion and a tetrahexylammonium ion; and a cyclic ammonium ion such as a 1,3-dimethylimidazolium ion, a 1,1-di-n-butylpyrrolidium ion, a piperidinium ion and a piperazium ion.

In Formula (1), $R_1$ and $R_2$ each independently represent a hydrogen atom, an aliphatic hydrocarbon residue which may have a substituent or an alkoxyl group which may have a substituent; and when $n_1$ is 2 or more, or, $m_1$ is 2 and $R_1$ and $R_2$ each exist in a plural number, then each $R_1$ and $R_2$ may be the same or different from each other; and a plural of $R_1$ and/or $R_2$ may form a ring, and further may have a substituent on this ring. Preferable examples of $R_1$ and $R_2$ include a hydrogen atom or an aliphatic hydrocarbon residue which may have a substituent. $R_1$ and $R_2$ are more preferably a hydrogen atom. The "aliphatic hydrocarbon residue which may have a substituent" and the "alkoxyl group" may be the same as those stated in the foregoing section of $X_1$.

In Formula (1), $R_3$ and $R_4$ each independently represent a hydrogen atom, an aliphatic hydrocarbon residue which may have a substituent or an aromatic hydrocarbon residue which may have a substituent, preferably an aliphatic hydrocarbon residue which may have a substituent, more preferably a saturated alkyl group which may have a substituent, further preferably a straight alkyl group of 1 to 6 carbon atoms, particularly preferably a straight alkyl group of 3 to 5 carbon atoms, most preferably an n-butyl group. When $m_1$ is 2 and $R_3$ and $R_4$ each exist in a plural number, then each $R_3$ and $R_4$ may be the same or different from each other; and $R_3$ and $R_4$ may be combined each other to form a ring which may have a substituent. Examples of the ring formed by combining $R_3$ and $R_4$ together include an aliphatic hydrocarbon ring which may have a substituent, and a heterocyclic ring which may have a substituent. The "aliphatic hydrocarbon residue which may have a substituent" and the "aromatic hydrocarbon residue which may have a substituent" may be the same as those stated in the section of $X_1$.

In view of solubility to a solvent which is used when a dye is carried on an oxide semiconductor fine particle, a suppressive effect against intermolecular aggregation, and the like, $R_1$, $R_2$, $R_3$ and $R_4$ in Formula (1) are appropriately selected.

Examples of the above "aliphatic hydrocarbon ring" include a saturated hydrocarbon ring such as a cyclobutane ring, a cyclopentane ring, a cyclohexane ring and a cycloheptane ring; and an unsaturated hydrocarbon ring such as a cyclobutene ring, a cyclopentene ring and a cyclohexene ring, which may further have a substituent.

Examples of the above "heterocyclic ring" include a 1,3-dioxane ring, a 1,3-dithiane ring, a 1,3-dioxolane ring, a 2,3,4,5-tetrahydropyridine ring, a 3,4,5,6-tetrahydropyridazine ring and a 5,5-dimethyl-1,3-dioxane ring.

In Formula (1), an aromatic ring a, an aromatic ring b and an aromatic ring e may further have 1 to 3, and an aromatic ring f may further have 1 to 4 substituents other than those clearly described in Formula (1), respectively. When $m_1$ in Formula (1) is 1, then either of an aromatic ring c or an aromatic ring d may further have 1 to 3, and the other may further have 1 to 4 substituents other than those clearly described in Formula (1), respectively. When $m_1$ is 2, then an aromatic ring c and an aromatic ring d may further have 1 to 3 substituents other than those clearly described in Formula (1), respectively. The substituent which the aromatic rings a, b, c, d and e, and the aromatic ring f may further have may be the same as those stated in the section of $X_1$.

Among the metal complex dyes represented by Formula (1), a metal complex dye represented by following Formula (2) or Formula (3) is preferred.

(2)

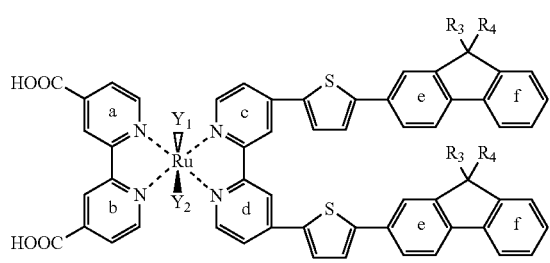

(3)

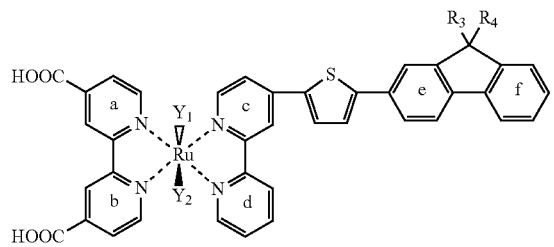

$Y_1$, $Y_2$, $R_3$ and $R_4$ in Formula (2) and Formula (3) are the same as $Y_1$, $Y_2$, $R_3$ and $R_4$ in Formula (1), respectively. The aromatic ring a to the aromatic ring f may have a substituent described in the explanation of Formula (1).

When the metal complex dyes represented by Formula (1) have an acidic group such as a carboxyl group, a phosphate group, a hydroxyl group and a sulfonate group as a substituent, they may form a salt, respectively. Examples of the salt include a salt with alkaline metal or alkaline earth metal etc. such as lithium, sodium, potassium, magnesium and calcium; or a salt with an organic base such as a quaternary ammonium such as tetramethylammonium, tetrabutylammonium, pyridinium, imidazolium, piperazinium and piperidinium. A tetrabutylammonium salt and a piperidinium salt are preferred.

The metal complex dye represented by Formula (1) may be a structural isomer such as a cis isomer, a trans isomer and a mixture thereof, an optically active substance and racemate, but not particularly limited to any isomer, and can be used well as a photosensitizing dye in the present invention.

The metal complex dye represented by Formula (1) can be produced, for example, by a reaction scheme shown below. That is to say, a compound of Formula (7) can be obtained by converting a bromofluorene form represented by following Formula (4) to a substituted form of Formula (5) by an alkylating agent etc., further followed by a coupling reaction with a boronic acid form (6). The compound of Formula (7) is brominated by NBS (N-bromosuccinimide) to give a compound of Formula (8). Compounds represented by Formulas (11) and (12) can be obtained by reacting this compound of Formula (8) with a pyridine derivatives (9) and (10). A compound of Formula (11) and a compound of Formula (12) can be condensed in accordance with a method described in Non Patent Document 4 to give a compound of Formula (13). The compound of Formula (13) and a ruthenium-p-cymene dimer (14) are reacted to obtain a compound of Formula (15), and further, the compound of Formula (15) is reacted with a bipyridine form represented by Formula (16) and ammonium thiocyanate of Formula (17) to obtain the metal complex dye represented by Formula (1).

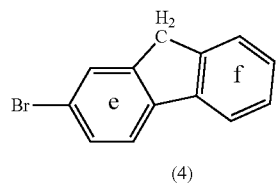
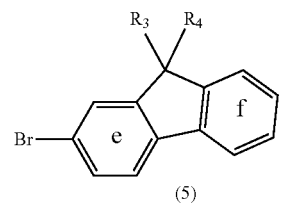
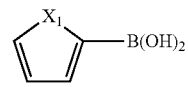
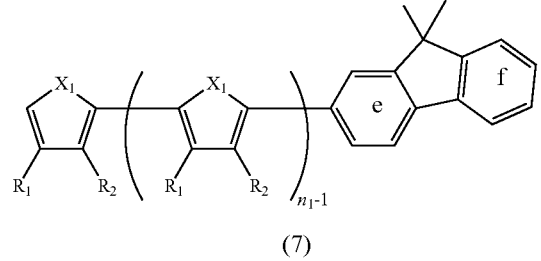
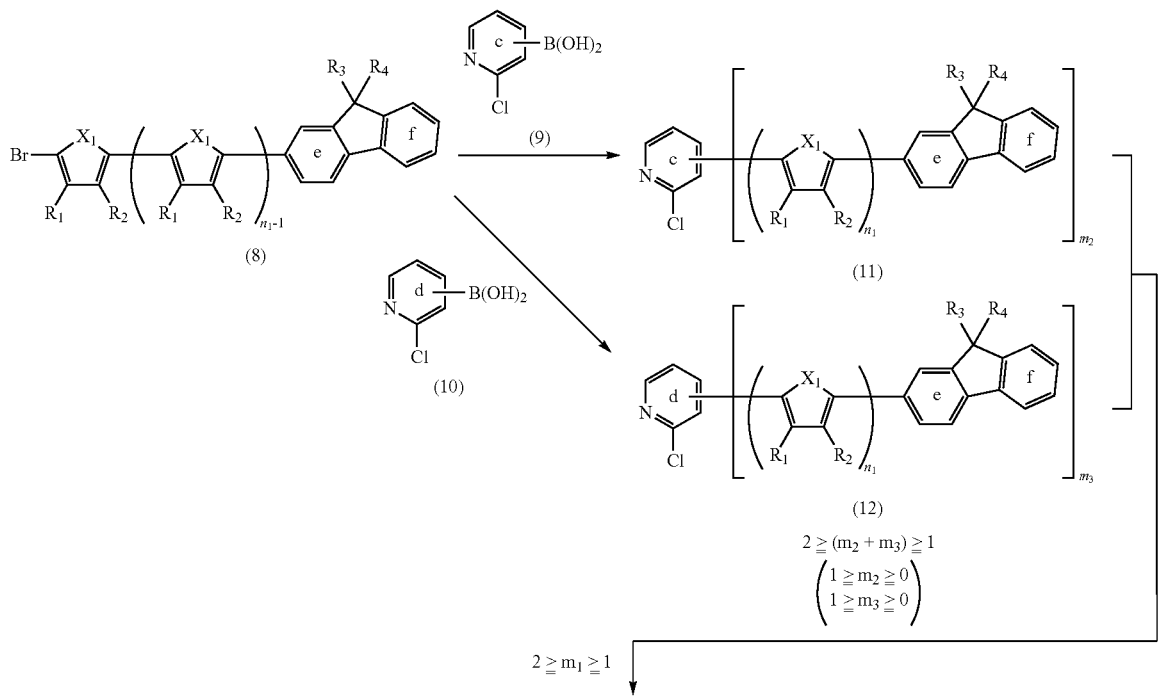
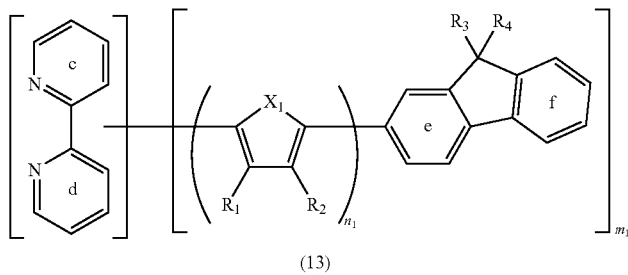

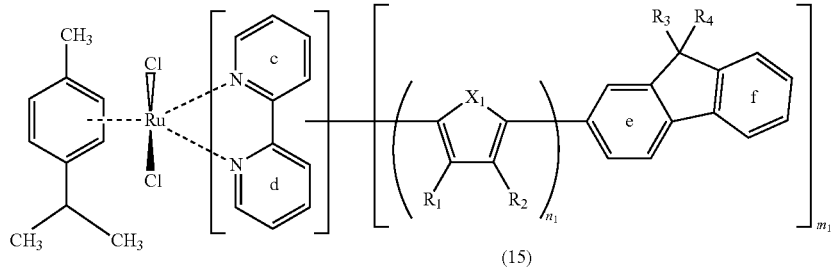

(15)

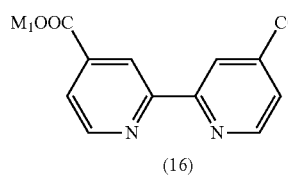

(16)

NH₄NCS
(17)

↓

(1)

In the following, preferred specific examples of the metal complex dye represented by Formula (1) are exemplified by following Formula (18). Preferred combinations of substituents and the like in Formula (18) are shown in Tables 1 to 2.

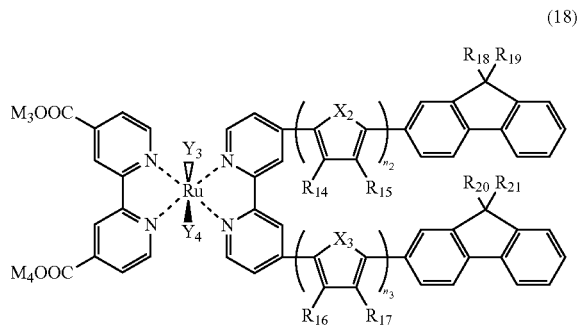

(18)

TABLE 1

| | $M_3$ $M_4$ | $n_2$ $n_3$ | $Y_3$ $Y_4$ | $X_2$ $X_3$ | $R_{14}$ $R_{18}$ | $R_{15}$ $R_{19}$ | $R_{16}$ $R_{20}$ | $R_{17}$ $R_{21}$ |
|---|---|---|---|---|---|---|---|---|
| 1 | H | 1 | Cl | O | H | H | H | H |
|   | H | 1 | Cl | O | H | H | H | H |
| 2 | H | 1 | Cl | S | H | H | H | H |

TABLE 1-continued

| | $M_3$ $M_4$ | $n_2$ $n_3$ | $Y_3$ $Y_4$ | $X_2$ $X_3$ | $R_{14}$ $R_{18}$ | $R_{15}$ $R_{19}$ | $R_{16}$ $R_{20}$ | $R_{17}$ $R_{21}$ |
|---|---|---|---|---|---|---|---|---|
|    | H  | 1 | Cl  | S  | H | H | H | H |
| 3  | H  | 1 | Cl  | S  | H | H | H | H |
|    | H  | 1 | Cl  | S  | CH₃ | CH₃ | CH₃ | CH₃ |
| 4  | H  | 1 | NCS | S  | H | H | H | H |
|    | H  | 1 | NCS | S  | CH₃ | CH₃ | CH₃ | CH₃ |
| 5  | H  | 1 | NCS | S  | H | H | H | H |
|    | H  | 1 | NCS | S  | C₂H₅ | C₂H₅ | C₂H₅ | C₂H₅ |
| 6  | H  | 1 | NCS | S  | H | H | H | H |
|    | H  | 1 | NCS | S  | n-C₄H₉ | n-C₄H₉ | n-C₄H₉ | n-C₄H₉ |
| 7  | H  | 1 | NCS | S  | H | H | H | H |
|    | H  | 1 | NCS | S  | Sec-C₄H₉ | sec-C₄H₉ | sec-C₄H₉ | sec-C₄H₉ |
| 8  | H  | 1 | NCS | S  | H | H | H | H |
|    | H  | 1 | NCS | S  | Tert-C₄H₉ | tert-C₄H₉ | tert-C₄H₉ | tert-C₄H₉ |
| 9  | Li | 1 | NCS | S  | H | H | H | H |
|    | Li | 1 | NCS | S  | n-C₅H₁₁ | n-C₅H₁₁ | n-C₅H₁₁ | n-C₅H₁₁ |
| 10 | K  | 1 | NCS | S  | H | H | H | H |
|    | K  | 1 | NCS | S  | n-C₆H₁₃ | n-C₆H₁₃ | n-C₆H₁₃ | n-C₆H₁₃ |
| 11 | H  | 1 | NCS | S  | H | H | H | H |
|    | H  | 1 | NCS | S  | n-C₈H₁₇ | n-C₈H₁₇ | n-C₈H₁₇ | n-C₈H₁₇ |
| 12 | H  | 1 | NCS | S  | H | H | H | H |
|    | H  | 1 | NCS | S  | n-C₁₈H₃₇ | n-C₁₈H₃₇ | n-C₁₈H₃₇ | n-C₁₈H₃₇ |
| 13 | H  | 1 | NCS | S  | H | H | H | H |
|    | H  | 1 | NCS | S  | n-C₄H₉ | CH₃ | n-C₄H₉ | CH₃ |
| 14 | H  | 1 | NCS | Se | H | H | H | H |
|    | H  | 1 | NCS | Se | n-C₄H₉ | n-C₄H₉ | n-C₄H₉ | n-C₄H₉ |
| 15 | H  | 1 | NCS | S  | CH₃ | CH₃ | CH₃ | CH₃ |
|    | H  | 1 | NCS | S  | n-C₄H₉ | n-C₄H₉ | n-C₄H₉ | n-C₄H₉ |

TABLE 2

| | $M_3$ $M_4$ | $n_2$ $n_3$ | $Y_3$ $Y_4$ | $X_2$ $X_3$ | $R_{14}$ $R_{18}$ | $R_{15}$ $R_{19}$ | $R_{16}$ $R_{20}$ | $R_{17}$ $R_{21}$ |
|---|---|---|---|---|---|---|---|---|
| 16 | H | 1 | NCS | S | n-C₆H₁₃ | H | n-C₆H₁₃ | H |
|    | H | 1 | NCS | S | n-C₄H₉ | n-C₄H₉ | n-C₄H₉ | n-C₄H₉ |
| 17 | H | 1 | NCS | S | H | n-C₆H₁₃ | H | n-C₆H₁₃ |
|    | H | 1 | NCS | S | n-C₄H₉ | n-C₄H₉ | n-C₄H₉ | n-C₄H₉ |

TABLE 2-continued

| | | | | | Compound | | | |
|---|---|---|---|---|---|---|---|---|
| | $M_3$ $M_4$ | $n_2$ $n_3$ | $Y_3$ $Y_4$ | $X_2$ $X_3$ | $R_{14}$ $R_{18}$ | $R_{15}$ $R_{19}$ | $R_{16}$ $R_{20}$ | $R_{17}$ $R_{21}$ |
| 18 | H | 1 | NCS | S | n-$C_6H_{13}$ | n-$C_6H_{13}$ | n-$C_6H_{13}$ | n-$C_6H_{13}$ |
| | H | 1 | NCS | S | n-$C_4H_9$ | n-$C_4H_9$ | n-$C_4H_9$ | n-$C_4H_9$ |
| 19 | Na | 1 | NCS | S | H | H | H | H |
| | Na | 1 | NCS | S | n-$C_4H_9$ | n-$C_4H_9$ | n-$C_4H_9$ | n-$C_4H_9$ |
| 20 | H | 1 | NCS | S | H | H | H | H |
| | H | 2 | NCS | S | n-$C_4H_9$ | n-$C_4H_9$ | n-$C_4H_9$ | n-$C_4H_9$ |
| 21 | H | 2 | NCS | S | H | H | H | H |
| | H | 2 | NCS | S | n-$C_4H_9$ | n-$C_4H_9$ | n-$C_4H_9$ | n-$C_4H_9$ |
| 22 | H | 1 | NCS | S | H | H | H | H |
| | H | 1 | NCS | S | $C_2H_4Cl$ | $C_2H_4Cl$ | $C_2H_4Cl$ | $C_2H_4Cl$ |
| 23 | H | 1 | NCS | S | H | H | H | H |
| | H | 1 | NCS | S | $CF_3$ | $CF_3$ | $CF_3$ | $CF_3$ |
| 24 | H | 1 | NCS | S | H | H | H | H |
| | H | 1 | NCS | S | n-$C_4F_9$ | n-$C_4F_9$ | n-$C_4F_9$ | n-$C_4F_9$ |
| 25 | H | 1 | NCS | S | H | H | H | H |
| | H | 1 | NCS | S | $C_2H_4OCH_3$ | $C_2H_4OCH_3$ | $C_2H_4OCH_3$ | $C_2H_4OCH_3$ |
| 26 | H | 1 | NCS | S | $CH_2Cl$ | $CH_2Cl$ | $CH_2Cl$ | $CH_2Cl$ |
| | H | 1 | NCS | S | n-$C_4H_9$ | n-$C_4H_9$ | n-$C_4H_9$ | n-$C_4H_9$ |
| 27 | H | 1 | NCS | S | $CF_3$ | $CF_3$ | $CF_3$ | $CF_3$ |
| | H | 1 | NCS | S | n-$C_4H_9$ | n-$C_4H_9$ | n-$C_4H_9$ | n-$C_4H_9$ |
| 28 | H | 2 | NCS | S | $CH_3$ | $CH_3$ | $CH_3$ | $CH_3$ |
| | H | 2 | NCS | S | n-$C_4H_9$ | n-$C_4H_9$ | n-$C_4H_9$ | n-$C_4H_9$ |
| 29 | H | 3 | NCS | S | H | H | H | H |
| | H | 3 | NCS | S | n-$C_4H_9$ | n-$C_4H_9$ | n-$C_4H_9$ | n-$C_4H_9$ |
| 30 | H | 1 | NCS | S | $OCH_3$ | H | $OCH_3$ | H |
| | H | 1 | NCS | S | n-$C_4H_9$ | n-$C_4H_9$ | n-$C_4H_9$ | n-$C_4H_9$ |

Other specific examples are shown below.

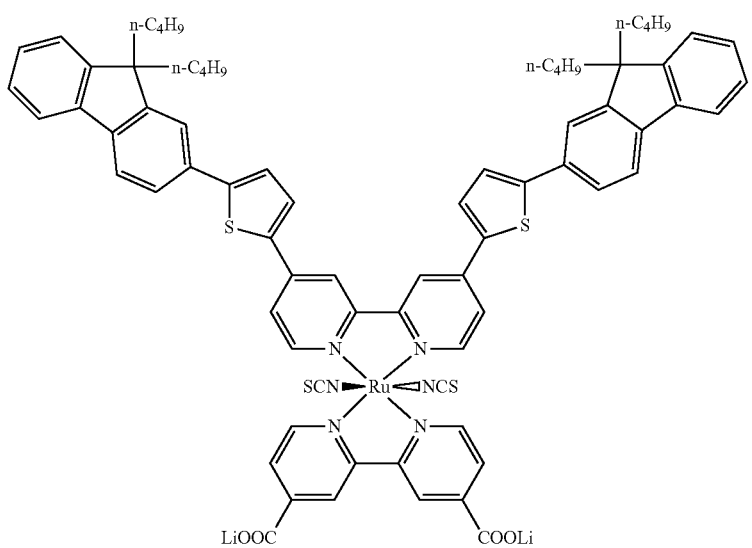

(31)

(32)
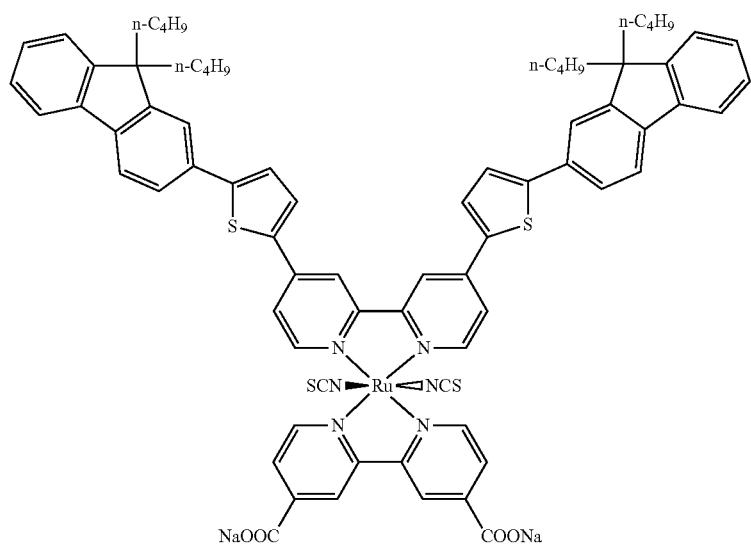
(33)
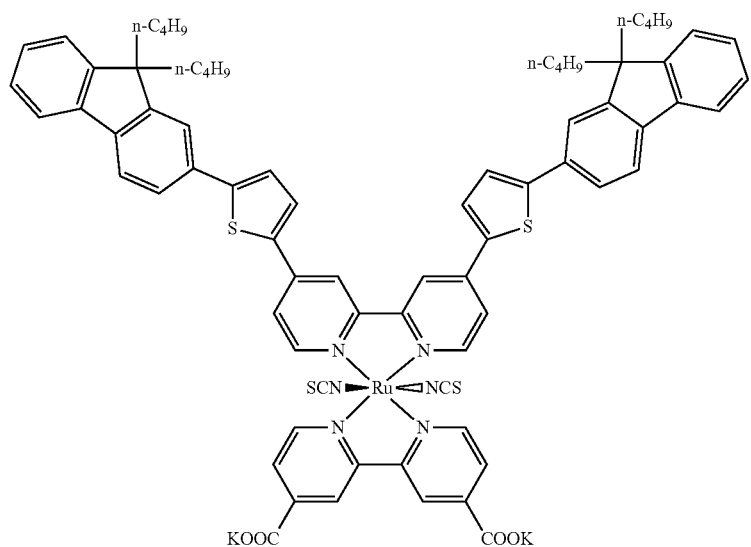

(34)
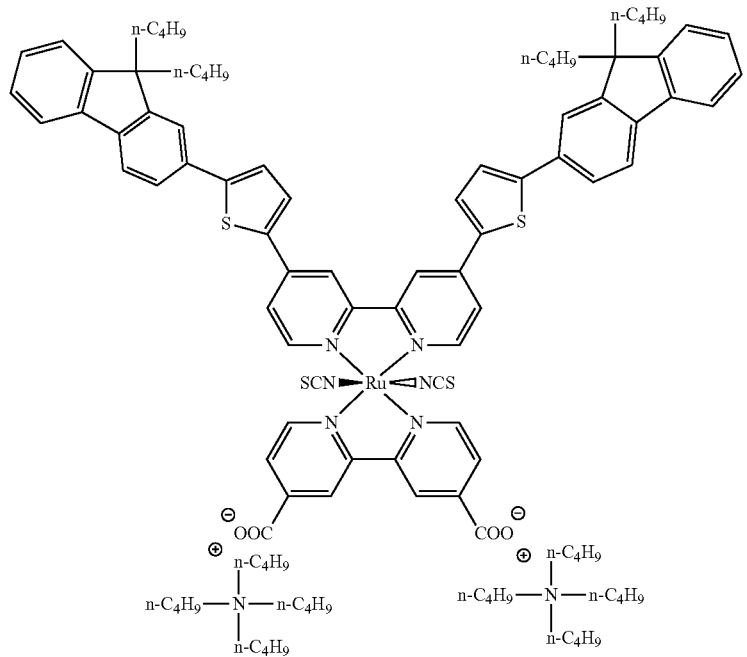
(35)
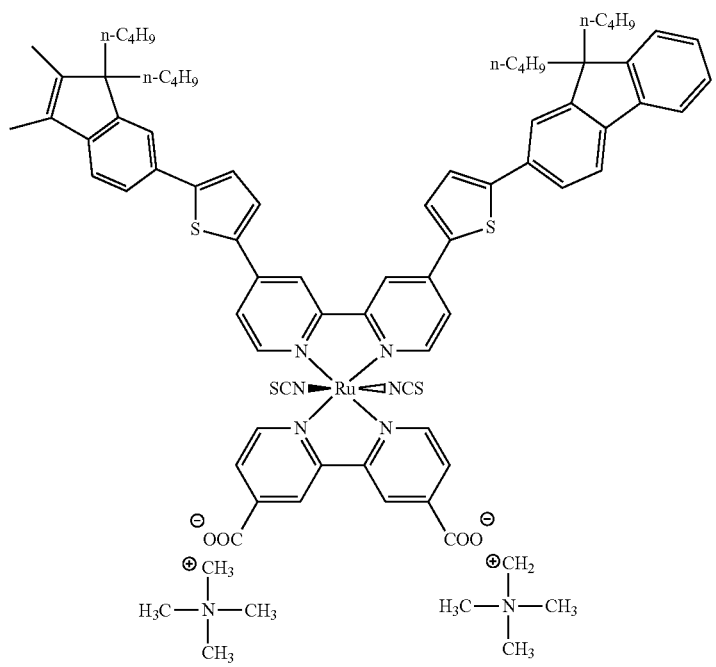

(36)
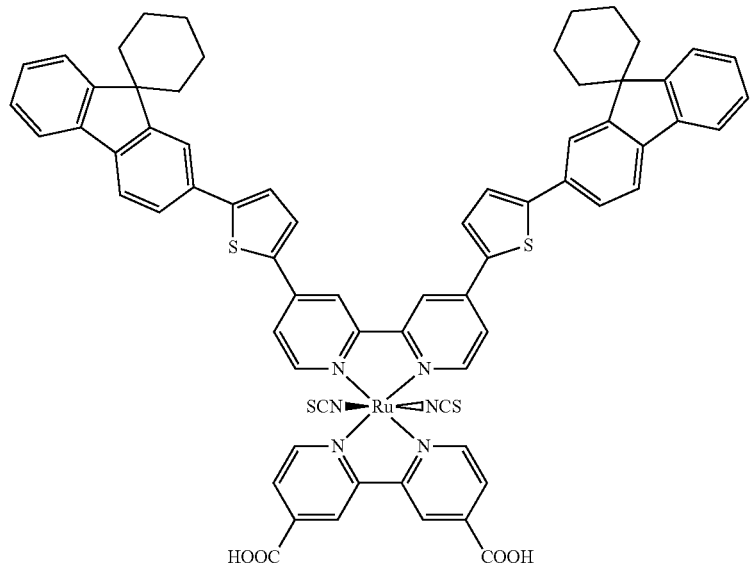
(37)
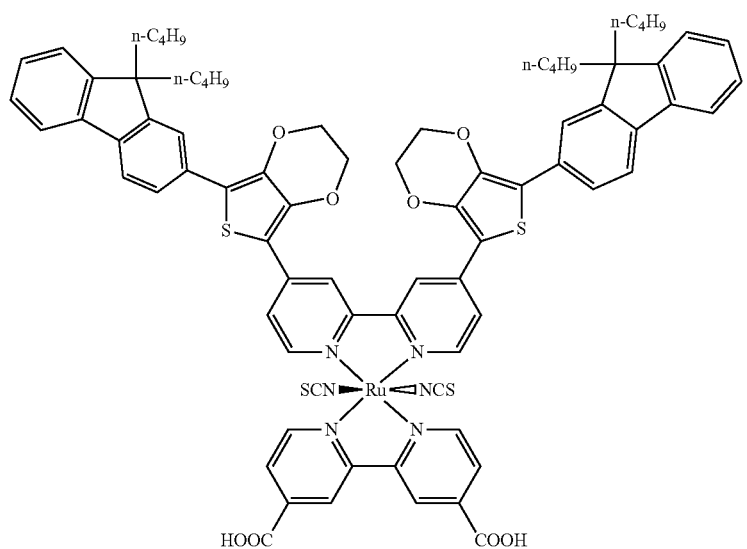

(38)
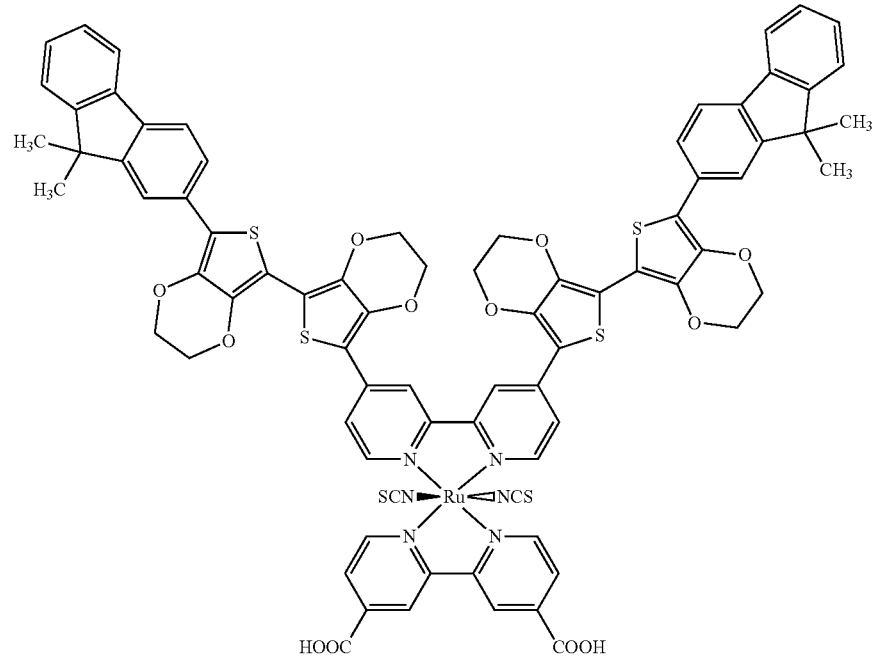
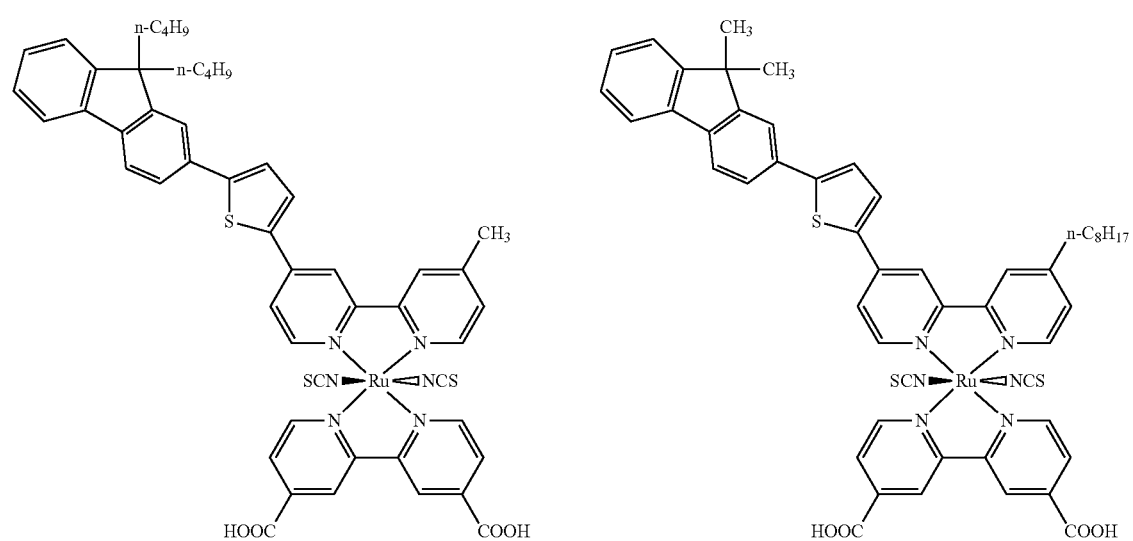

-continued
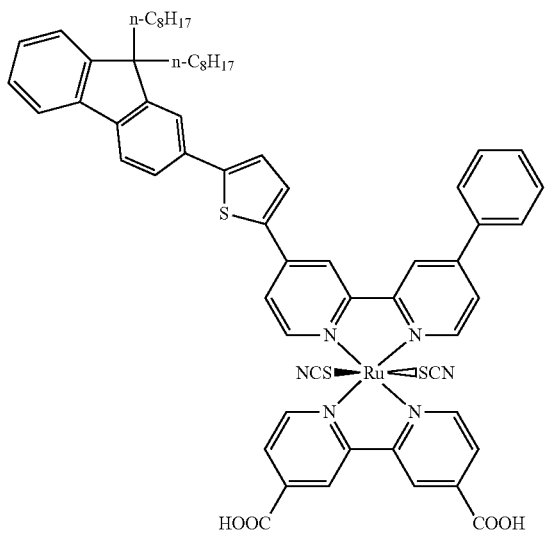
(41)
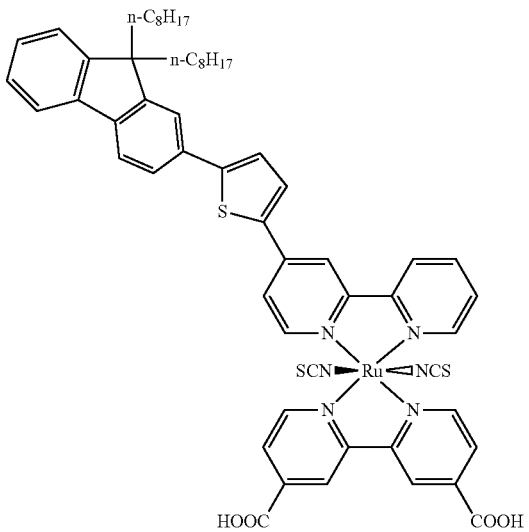
(42)
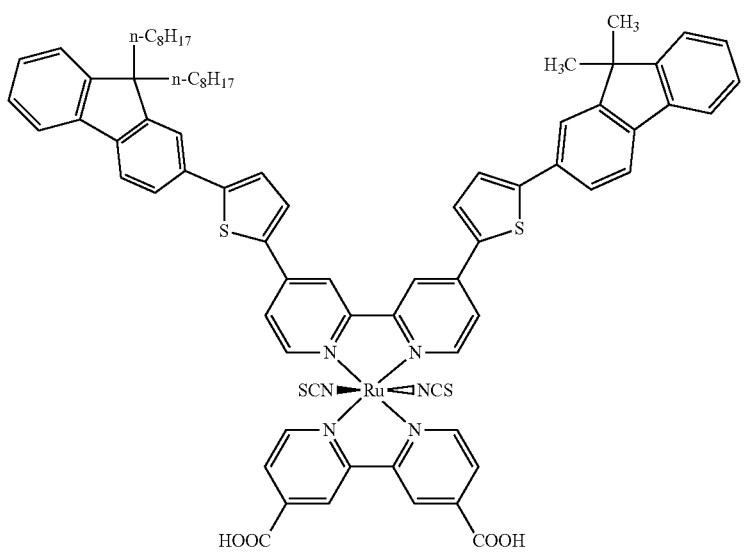
(43)

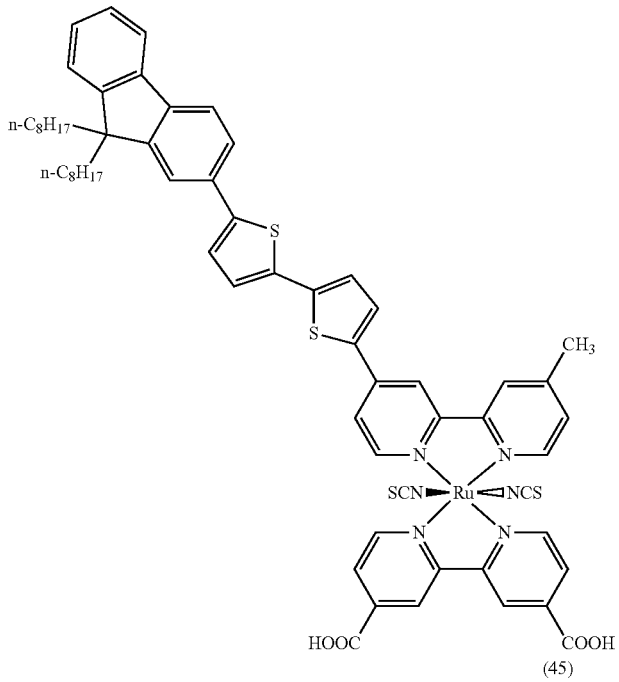

(44)

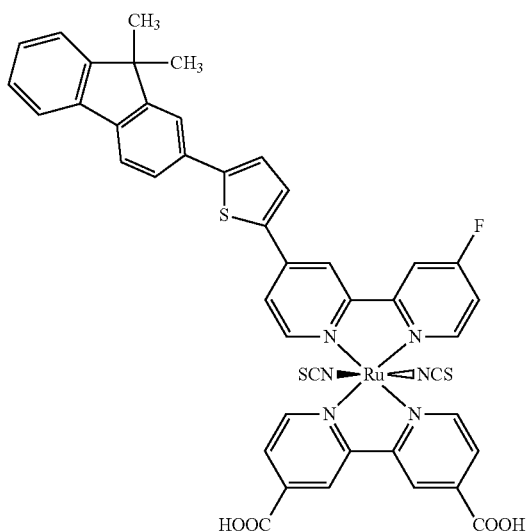

(45)

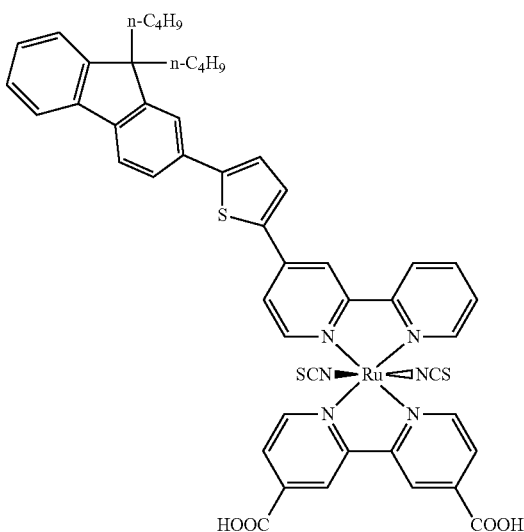

(46)

The dye-sensitized photoelectric conversion device of the present invention is, for example, a device in which a thin film of oxide semiconductor fine particles is disposed on a substrate by using the oxide semiconductor fine particle, and then the metal complex dye of Formula (1) is carried on this thin film.

In the present invention, a substrate having a conductive surface is preferable as the substrate on which the thin film of oxide semiconductor fine particles is disposed. Such a substrate is commercially easily available. Specifically, for example, a substrate formed by disposing a thin film of a conductive metal oxide such as tin oxide doped with indium, fluorine, or antimony, or a metal thin film of copper, silver or gold on a glass surface or a surface of a transparent polymer material such as polyethylene terephthalate or polyethersulfone can be used. The conductivity may be usually 1,000Ω or less, particularly preferably 100Ω or less. A metal oxide is preferable as the fine particle of the oxide semiconductor. Examples of the metal oxide include oxides of titanium, tin, zinc, tungsten, zirconium, gallium, indium, yttrium, niobium, tantalum, vanadium and the like. Among them, the oxides of titanium, tin, zinc, niobium, indium and the like are preferable, and titanium oxide, zinc oxide and tin oxide are more preferable. These oxide semiconductors can be used alone, but also can be used in mixture or by being coated on a surface of a semiconductor. The particle size of the oxide semiconductor fine particle is usually 1 to 500 nm as an average particle size, preferably 1 to 100 nm. This oxide semiconductor fine particle can be used by mixing a particle of a large particle size and a particle of a small particle size, or in a multilayer.

The thin film of oxide semiconductor fine particles can be formed on a substrate by a method in which the oxide semiconductor fine particle is directly applied by spraying or the like on the substrate, a method in which the semiconductor fine particle is electrically deposited on the substrate as an electrode in a form of a thin film, a method in which a slurry of semiconductor fine particles, or a paste containing a fine particle obtained by hydrolyzing a precursor of a semiconductor fine particle such as semiconductor alkoxide is applied on the substrate followed by drying, hardening or calcification, and the like. The method using the slurry is preferable in view of the performance of the electrode using the oxide semiconductor. In this method, the slurry can be obtained by conventionally dispersing secondary coagulated oxide semiconductor fine particles in a dispersion medium so that an average primary particle size is 1 to 200 nm.

The dispersion medium in which the slurry is dispersed is not particularly limited as long as it can disperse the semiconductor fine particles therein. Water, alcohol such as ethanol, ketone such as acetone and acetylacetone, hydrocarbon such as hexane and the like may be used. They may be used in mixture, and use of water is preferable because the viscosity change of the slurry is reduced. In order to stabilize the dispersed condition of the oxide semiconductor fine particles, a dispersion stabilizer can be used. Examples of the dispersion stabilizer which can be used include an acid such as acetic acid, hydrochloric acid and nitric acid, or an organic solvent such as acetylacetone, an acrylic acid, polyethylene glycol and polyvinyl alcohol.

A substrate on which the slurry was applied may be calcined, the calcification temperature is usually 100° C. or higher, preferably 200° C. or higher, and the upper limit is approximately the melting point (softening point) of the substrate or lower, usually the upper limit is 900° C., preferably 600° C. or lower. The calcification time is not particularly limited, but is preferably approximately within 4 hours. The thickness of the thin film of oxide semiconductor fine particles on the substrate is usually 1 to 200 μm, preferably 1 to 50 μm.

A secondary treatment may be applied to the thin film of oxide semiconductor fine particles. For example, the whole substrate on which the thin film of oxide semiconductor fine particles is disposed may be directly immersed into a solution of an alkoxide, a metal acyloxide, a chloride, a nitride, a sulfide etc. of the metal same as the semiconductor followed by drying or recalcination in order to improve performance of the thin film of semiconductor fine particles. Examples of the metal alkoxide include titanium ethoxide, titanium isopropoxide and titanium t-butoxide, and examples of the metal acyloxide include n-dibutyl-diacetyltin. When using them, their alcohol solutions are usually used. Examples of the chloride include titanium tetrachloride, tin tetrachloride and zinc chloride. When using them, their aqueous solutions are usually used.

The thus obtained oxide semiconductor thin film is comprised of fine particles of an oxide semiconductor.

Next, a method in which the metal complex dye represented by Formula (1) of the present invention is carried on a thin film of oxide semiconductor fine particles will be described below.

As the method in which the metal complex dye of Formula (1) is carried, a method in which a substrate on which the thin film of oxide semiconductor fine particles is disposed is immersed in a solution obtained by dissolving a metal complex dye in a solvent capable of dissolving the metal complex dye, or in the case of a low soluble metal complex dye, by dissolving a metal complex dye in a dispersion obtained by dispersing the metal complex dye therein can be mentioned. The immersion temperature is approximately from room temperature to the boiling point of the solvent, and the immersion time is around 1 minute to 48 hours. Specific examples of the solvent which can be used for dissolving the metal complex dye include methanol, ethanol, acetonitrile, dimethylsulfoxide, dimethylformamide, acetone and t-butanol. These solvents can be used by mixing two or more of them at an optional ratio. When the metal complex dye of Formula (1) does not show sufficient solubility in these solvents, an ammonium salt such as tetrabutylammonium iodide can be added in order to promote dissolution of the dye. The concentration of the metal complex dye in the solution or dispersion may be appropriately determined depending on the metal complex dye, but usually the concentration is $1\times10^{-6}$ M to 1 M, preferably $1\times10^{-5}$ M to $1\times10^{-1}$ M. In this way, the photoelectric conversion device of the present invention having the thin film of oxide semiconductor fine particles sensitized with the metal complex dye of Formula (1) can be obtained.

The metal complex dye of Formula (1) to be carried may be one kind or a mixture of several kinds. When it is a mixture, the mixture may be made by mixing a metal complex dye of Formula (1) of the present invention and another metal complex dye of Formula (1) of the present invention, or other metal complex dyes or an organic dye can be admixed. In particular, mixture of metal complex dyes having different absorption wavelengths enables utilization of a wide range of absorption wavelengths, producing a solar cell of a high conversion efficiency. As the metal complex dye which can be mixed with the metal complex dye represented by Formula (1) of the present invention, without a special limitation, a ruthenium complex shown in Non Patent Document 2 and a quaternary salt thereof, phthalocyanine, porphyrin and the like are preferred. Examples of the organic dye used in mixture include dyes such as metal-free phthalocyanine, porphyrin and cyanine, merocyanine, oxonol, triphenylmethane types, a methine dye such as an acrylic acid dye shown in Patent Document 2, a xanthene type, an azo type, an anthraquinone type and a perylene type. Preferably, a ruthenium complex, merocyanine or a methine dye such as acrylic acid dye, and the like are included. When two or more of dyes are used, these dyes may be adsorbed sequentially on a thin film of semiconductor fine particles or adsorbed after mixing and dissolving them.

The mixing ratio of these dyes is not particularly limited, and the optimal condition is appropriately selected depending on each of the dyes and is preferably from equal molar ratio to at least not less than about 10% by mole per one dye. When a dye is subjected to adsorption on a film of oxide semiconductor fine particles using a solution in which two or more dyes are dissolved or dispersed, the total concentration of the dyes in the solution may be similar to that in carrying only one kind. As a solvent when dyes are used in mixture, such a solvent as described above can be used and the solvents for each dye to be used may be the same or different.

When a metal complex dye is carried on a thin film of oxide semiconductor fine particles, in order to prevent aggregation of metal complex dyes themselves, it is effective to carry the metal complex dyes in the presence of a chlathrate compound. In this case, examples of the chlathrate compound include a steroid type compound such as cholic acid, crown ether, cyclodextrin, calixarene and polyethylene oxide, and preferably include cholic acid derivatives such as deoxycholic acid, dehydrodeoxycholic acid, chenodeoxycholic acid, cholic acid methyl ester and cholic acid sodium salts; polyethylene oxide, etc. After carrying of a metal complex dye, the thin film of semiconductor fine particles may be treated with an amine compound such as 4-tert-butylpyridine (TBP). A method for treatment includes, for example, a method for dipping a substrate formed with a thin film of semiconductor fine particles carrying a metal complex dye, in an ethanol solution of an amine.

A solar cell of the present invention is composed of an electrode of a photoelectric conversion device in which a metal complex dye is carried on a thin film of the above oxide semiconductor fine particles, a counter electrode, a redox electrolyte or a positive hole transportation material or a p-type semiconductor, and the like. Morphologies of the redox electrolyte, the positive hole transportation material, the p-type semiconductor and the like include liquid, a solidified substance (gel or gel-like substance), a solid and the like. The liquid-like morphology includes a solution of a redox electrolyte, a molten salt, a positive hole transportation material, a p-type semiconductor and the like in a solvent, a molten salt at normal temperature and the like. The solidified substance morphology (gel or gel-like substance) includes those containing these in polymer matrix or a low molecular weight gelling agent and the like. As the solid morphology, a redox electrolyte, a molten salt, a positive hole transportation material, a p-type semiconductor and the like can be used. The positive hole transporting material includes amine derivatives; conductive polymers such as polyacetylene, polyaniline and polythiophene; and those used for discotic liquid crystals such as a triphenylene type compound. The p-type semiconductor includes CuI, CuSCN and the like.

As the counter electrode, such one is preferable as has conductivity and acts catalytically for reduction reaction of the redox electrolyte. Such one can be used as glass or a polymer film on which platinum, carbon, rhodium, ruthenium and the like are vapor depositioned or conductive fine particles are applied.

The redox electrolyte used for a solar cell of the present invention includes a halogen redox-type electrolyte comprising a halogen compound having a halogen ion as a counter ion and a halogen molecule; a metal redox-type electrolyte of a metal complex etc. such as a ferrocyanide-ferricyanide salt or a ferrocene-ferricinium ion and a cobalt complex; an organic redox-type electrolyte such as an alkyl thiol-alkyl disulfide, a viologen dye, hydroquinone-quinone, and a halogen redox-type electrolyte is preferable. In the halogen redox-type electrolyte comprising a halogen compound and a halogen molecule, examples of the halogen molecule include such as an iodine molecule and a bromine molecule, and an iodine molecule is preferable. Examples of the halogen compound having a halogen ion as a counter ion include a salt of a metal halide such as LiBr, NaBr, KBr, LiI, NaI, KI, CsI, $CaI_2$, $MgI_2$, CuI; or an organic quaternary ammonium salt such as tetraalkylammonium iodide, imidazolium iodide and pyridinium iodide, and a salt having an iodide ion as a counter ion is preferable. Other than the above iodide ion, an electrolyte having an imide ion such as a bis(trifluoromethanesulfonyl) imide ion and a dicyanoimide ion as a counter ion is preferably used.

When the redox electrolyte takes a solution form containing it, an electrochemically inert solvent is used. The solvent includes, for example, acetonitrile, propylene carbonate, ethylene carbonate, 3-methoxypropionitrile, methoxyacetonitrile, ethylene glycol, propylene glycol, diethylene glycol, triethylene glycol, γ-butyrolactone, dimethoxyethane, diethyl carbonate, diethyl ether, diethyl carbonate, dimethyl carbonate, 1,2-dimethoxyethane, dimethylformamide, dimethylsulfoxide, 1,3-dioxolan, methyl formate, 2-methyltetrahydrofuran, 3-methyl-oxazolidine-2-one, sulpholane, tetrahydrofuran and water, and among them, acetonitrile, propylene carbonate, ethylene carbonate, 3-methoxypropionitrile, methoxyacetonitrile, ethylene glycol, 3-methyl-oxazolidine-2-one and γ-butyrolactone are particularly preferable.

These solvents may be used alone or in combination of two or more kinds. The gel-like electrolyte includes matrix such as an oligomer and a polymer containing the electrolyte or an electrolyte solution; a low molecular weight gelling agent described in Non Patent Document 3 and the like, similarly containing the electrolyte or an electrolyte solution, and the like. The concentration of the redox electrolyte is usually 0.01 to 99% by mass, preferably 0.1 to 90% by mass.

A solar cell of the present invention can be prepared by placing a counter electrode on an electrode of a photoelectric conversion device carrying a metal complex dye of Formula (1) of the present invention on a thin film of oxide semiconductor fine particles on a substrate so as to sandwich the thin film between the counter electrode and the electrode, and filling a space between them with a solution containing the redox electrolyte and the like.

EXAMPLES

The present invention is explained in more detail in reference to the following Examples, but the scope of the present invention should not be limited thereto. In Examples, "part" means "mass part" unless otherwise specified.

Absorption, nuclear magnetic resonance analysis and mass analysis were conducted by using a spectrophotometer UV-3150 (from Shimadzu Corporation), Gemini 300 (from Varian Inc.) and a high performance liquid chromatograph-mass spectrometer LCMS-2010EV (from Shimadzu Corporation), respectively.

Synthetic Example 1

Under a nitrogen atmosphere, to a solution obtained by dissolving 20.8 parts of potassium tert-butoxide in 102 parts of dimethylsulfoxide (DMSO), a solution obtained by dissolving 15.4 parts of 2-bromofluorene in 153 parts of dimethylsulfoxide (DMSO) was added dropwise. After stirring for 30 minutes, while keeping the reaction solution temperature to 40 to 45° C., 27.8 parts of butyl iodide was added dropwise. After stirring at 40° C. for 40 minutes, the reaction solution was added to ice water. The reaction mixture was extracted with chloroform-water, the chloroform phase was dried over magnesium sulfate, and then chloroform was distilled off to obtain a brown tarry solid. This brown tarry solid was dissolved in a small amount of chloroform, and separated and purified by column chromatography (hexane) to obtain 12.6 parts of 2-bromo-9,9-dibutylfluorene as a colorless crystal.

Synthetic Example 2

After dissolving 2.7 parts of 2-thiopheneboronic acid and 6 parts of 2-bromo-9,9-dibutylfluorene was dissolved in 78 parts of 1,2-dimethoxyethane, 0.59 part of tetrakis(triphenylphosphine)palladium(0) and 47 parts of a 20% sodium carbonate aqueous solution were added, and the mixture was reacted for 5 hours under reflux. The reaction mixture was extracted with toluene, and the toluene phase was dried over magnesium sulfate, and then toluene was distilled off to obtain a brown tarry mixture. The resultant brown tarry mixture was separated and purified by column chromatography (hexane-ethyl acetate) to obtain 5.9 parts of the following compound (1001) as a colorless crystal.

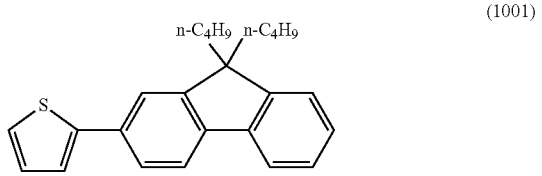

(1001)

Synthetic Example 3

After dissolving 5.9 parts of the above compound (1001) in 635 parts of a 1:1 mixed solution of chloroform and acetic acid, 1.9 parts of N-bromosuccinimide was added, and the mixture was reacted for one hour under reflux. After further adding 0.94 part of N-bromosuccinimide, the mixture was reacted for one hour under reflux. The reaction mixture was extracted with a 5% sodium hydrogencarbonate aqueous solution-chloroform, and the chloroform phase was dried over magnesium sulfate, and then chloroform was distilled off. The resultant mixture was separated and purified by column chromatography (hexane-ethyl acetate) to obtain 6.8 parts of the following compound (1002) as a colorless crystal.

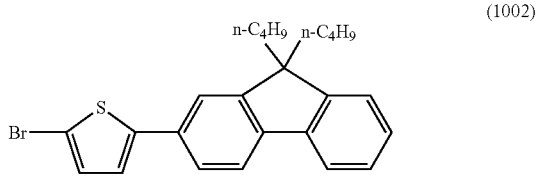

(1002)

Synthetic Example 4

After dissolving 5.0 parts of the above compound (1002) and 2.2 parts of 2-chloro-4-pyridineboronic acid in 40 parts of 1,2-dimethoxyethane, 0.38 part of tetrakis(triphenylphosphine)palladium(0) and 25 parts of a 20% sodium carbonate aqueous solution were added, and the mixture was reacted for 5 hours under reflux. The reaction mixture was extracted with chloroform, and the chloroform phase was dried over magnesium sulfate, and then chloroform was distilled off. The resultant mixture was separated and purified by column chromatography (chloroform) to obtain 5.0 parts of the following compound (1003) as a pale yellow solid.

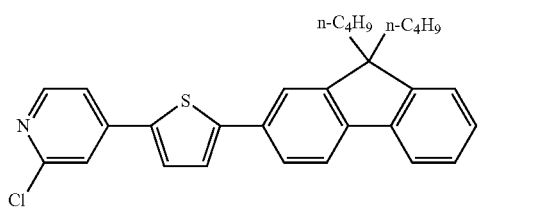

(1003)

Synthetic Example 5

Under a nitrogen atmosphere, 1.6 parts of dibromobis (triphenylphosphine)nickel(II), 1.2 parts of zinc powder, 0.78 part of lithium chloride and 2.7 parts of tetraethylammonium iodide were added to 39 parts of tetrahydrofuran, and the mixture was stirred. A solution obtained by dissolving 5.0 parts of the above compound (1003) in 20 parts of tetrahydrofuran was added dropwise, and the mixture was reacted for 20 hours under reflux. After cooling the reaction solution to room temperature, 44 parts of 30% ammonia water, 32 parts of water, 178 parts of dichloromethane were added, and the mixture was stirred for 15 minutes. The reaction mixture was extracted with dichloromethane, and the dichloromethane phase was dried over magnesium sulfate, and then dichloromethane was distilled off. The resultant mixture was separated and purified by column chromatography (chloroform) to obtain 3.3 parts of the following compound (1004) as a pale yellow solid.

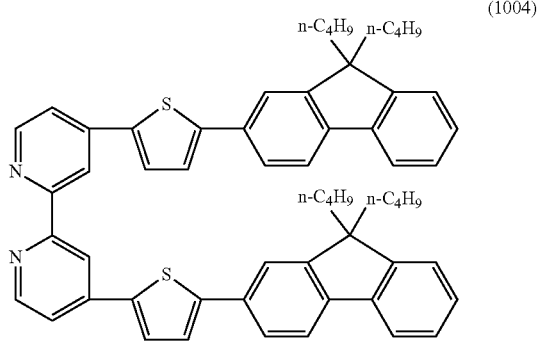

(1004)

Synthetic Example 6

Under a nitrogen atmosphere, 1 part of the above compound (1004) and 0.35 part of a ruthenium-p-cymene dimer were heated under reflux in 75 parts of chloroform. After completion of the reaction, chloroform was distilled off, and then dried at 60° C. for 14 hours to obtain 1.35 parts of the following compound (1005) as a brown crystal.

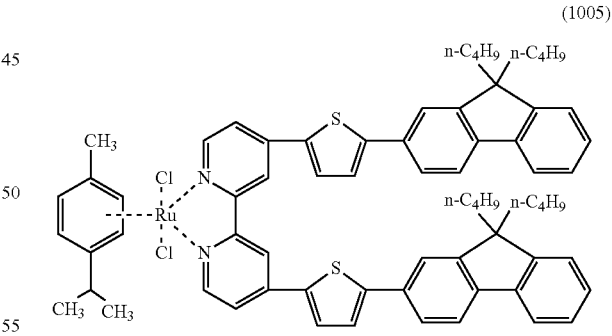

(1005)

Measured values from nuclear magnetic resonance analysis of this compound (1005) were as follows.

Measured values from nuclear magnetic resonance analysis;

$^1$H-NMR(PPM:d6-DMSO):0.515-0.562(m,6H),0.614-0.663(t,12H), 1.012-1.098(m,16H),2.086(m,8H),2.233(s,3H),2.634-2.728(m,1H), 6.020-6.040(d,2H),6.259-6.279(d,2H),7.364-7.392(m,4H), 7.479-7.508(m,2H),7.821-7.953(m,10H),7.988-8.008(d,2H), 8.371-8.384(d,2H),9.045(s,2H),9.454-9.475(d,2H)

Example 1

Under light shielding and a nitrogen atmosphere, 0.521 part of the above compound (1005) and 0.099 part of 2,2'-bipyridine-4,4'-dicarboxylic acid were stirred at 140° C. for 4 hours in 20 parts of anhydrous dimethylformamide (DMF). 0.65 Part of ammonium thiocyanate was added, and the mixture was stirred for additional 4 hours. After completion of the reaction, the mixture was allowed to cool to room temperature, and to stand for 36 hours. Afterward, the reaction solution was filtered, and the filtrate was poured into 100 parts of water, and the precipitated crystals were filtered off. The resultant crystals were washed twice with 2 parts of water, and then dried at 70° C. for 14 hours to obtain 0.522 part of the compound (metal complex dye) of compound number (6) in the above Table 1 as a black brown crystal.

Measured values of absorption, nuclear magnetic resonance analysis and mass analysis of this compound number (6) were as follows.

Measurement of absorption

Maximum absorption wavelength ($\lambda$max)=388 nm, molecular extinction coefficient ($\epsilon$)=56625 (solvent: N,N-dimethylformamide)

This compound showed the maximum absorption wavelength at 553 nm.

Measured values from nuclear magnetic resonance analysis;

$^1$H-NMR(PPM:d6-DMSO):0.534-0.670(m,16H),0.989-1.083(m,12H),2.081(m,8H), 7.089-7.102(d,2H),7.361-7.461(m,8H),7.656-7.744(dd,2H), 7.843-7.950(m,8H), 8.155-8.384(m,4H),8.967-9.018(d,2H), 9.123-9.171(d,2H), 9.216-9.235(d,1H),9.459-9.478(d,1H)

Mass analysis measured value;
Mass (M-1)=1334

Example 2 and Comparative Example 1

A titanium oxide dispersion, PASOL HPW-18NR (from Shokubai Kasei Kogyo K.K.) was made into a paste, and was applied onto a transparent conductive glass electrode to form a titanium oxide film. To a semiconductor thin film obtained by sintering the titanium oxide film at 450° C. for 30 minutes, about 1 cc of a 0.04 M titanium tetrachloride aqueous solution was added dropwise followed by standing at 60° C. for 30 minutes and water washing, and then again calcination at 450° C. for 30 minutes to obtain a porous substrate having a titanium tetrachloride-treated semiconductor thin film (film thickness: 7 μm, measured by a surface roughness/shape measuring instrument Surfcom 570A from Tokyo Seimitu Co., Ltd.).

The metal complex dye of compound number (6) obtained in Example 1 was dissolved in a mixed solvent of tert-butanol:acetonitrile (1:1) so as to be 3.0×10$^{-4}$ M, and further chenodeoxycholic acid was added so as to be 40 mM. To this solution, the porous substrate obtained by the foregoing method was immersed at room temperature (20° C.) for 12 hours to make the substrate carry a dye, and then washed with the mixed solvent followed by drying to obtain a photoelectric conversion device of the present invention comprising a thin film of dye-sensitized semiconductor fine particles. In the same way, a photoelectric conversion device for comparison was obtained by using a compound represented by following Formula (2001) (see Example 2 of U.S. Pat. No. 3,731,752).

The solar cell of the present invention and the solar cell for comparison were obtained respectively by fixing oppositely the thin films of semiconductor fine particles of the photoelectric conversion device of the present invention and of the photoelectric conversion device for comparison thus obtained, and a sputtered surface of conductive glass sputtered with platinum with a void space of 20 micrometer therebetween, and filling the void space by pouring a solution containing an electrolyte. As the electrolyte, a 3-methoxypropionitrile solution of (1,2-dimethyl-3-propylimidazolium iodide 0.6 M)+(LiI 0.1M)+(I$_2$ 0.1 M)+(tert-butylpyridine 0.5 M) was used.

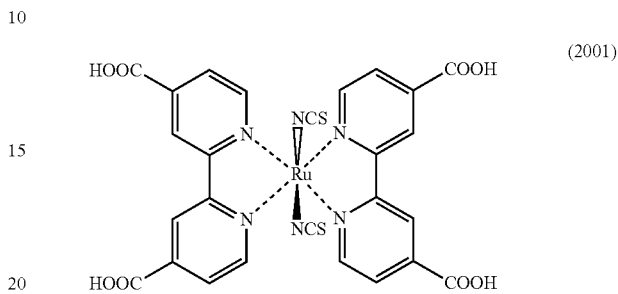

(2001)

The size of the efficient part of a cell to be measured was 0.25 cm$^2$. The light source was 100 mW/cm$^2$ through an AM (air mass) 1.5 filter. The short circuit current, the open circuit voltage, the conversion efficiency were measured by using solar simulator YSS-50A (from Yamashita Denso Co. Ltd.).

TABLE 3

Evaluation results

| | Compound Number | Open circuit voltage (V) | Short circuit current (mA/cm$^2$) | Conversion efficiency |
|---|---|---|---|---|
| Example 2 | (6) | 0.73 | 11.0 | 5.1 |
| Comparative Example 1 | (2001) | 0.69 | 2.6 | 1.3 |

In viewing the results of Table 3, an excellent photoelectric conversion efficiency was obtained from the compound of compound number (6), which efficiency is better than that of a known dye (2001). In particular, the compound of compound number (6) was confirmed to show a sufficiently high conversion efficiency even when the film thickness of titanium dioxide was thin.

The metal complex dye of the present invention is highly soluble in an organic solvent during a purification process or when being adsorbed on a titanium dioxide electrode, and therefore also has these excellent workability.

Synthetic Example 7

Under a nitrogen atmosphere, 4.7 parts of the above compound (1003) and 0.1 part of bis(tri-tert-butylphosphine)palladium(0) were added to 27 parts of tetrahydrofuran followed by stirring. 30 Parts of a solution of 2-pyridylzinc bromide in tetrahydrofuran (0.5 mol/L) was added dropwise, and the mixture was reacted for one hour under reflux. Further, 0.1 part of bis(tri-tert-butylphosphine)palladium(0) was added and refluxed for 2 hours, which was repeated twice. After cooling the reaction solution to room temperature, the reaction mixture was extracted with chloroform, and the chloroform phase was dried over magnesium sulfate, and then chloroform was distilled off. The resultant mixture was recrystallized with a chloroform/hexane mixed solution to obtain 4.5 parts of the following compound (1006) as a pale yellow solid.

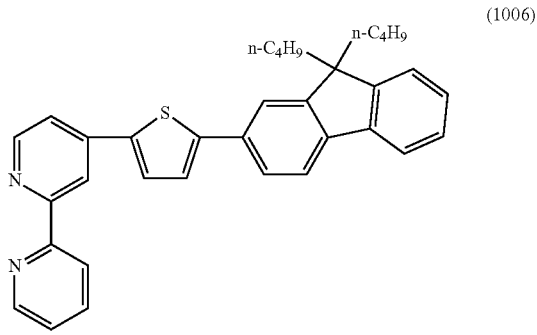

(1006)

Measured values from nuclear magnetic resonance analysis of this compound (1006) were as follows. Measured values from nuclear magnetic resonance analysis;
$^1$H-NMR(PPM:CD$_2$Cl$_2$):0.65(m.10H),1.15(m.4H),2.10(t.4H),7.41(m.4H),7.53(d.1H), 7.62(dd.1H),7.78(m.5H), 7.91(m.1H),8.53(d.1H),8.71(d.1H),8.76(m.2H)

Synthetic Example 8

Under a nitrogen atmosphere, 2.00 parts of the above compound (1006) and 1.19 parts of a ruthenium-p-cymene dimer were heated under reflux in 200 ml of chloroform for 4 hours. After completion of the reaction, chloroform was distilled off, and then dried at 60° C. for 14 hours to obtain 3.18 parts of the following compound (1007) as a brown crystal.

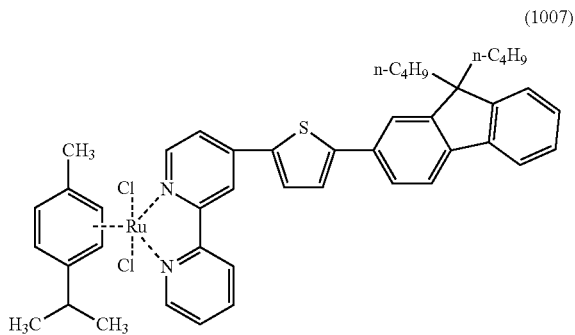

(1007)

Measured values from nuclear magnetic resonance analysis of this compound (1007) were as follows.
Measured values from nuclear magnetic resonance analysis;
$^1$H-NMR(PPM:d-DMSO):0.58(m.10H),1.03(m.10H), 2.06(m.4H),2.21(s.3H),2.61(m.1H), 6.01(d.2H),6.26(t.2H), 7.37(m.2H),7.48(m.1H),7.88(m.7H),8.35(m.2H),8.93(m.2H),9.51(dd.2H)

Example 3

Under light shielding and a nitrogen atmosphere, 3.00 parts of the above compound (1007) and 0.82 part of 2,2'-bipyridine-4,4'-dicarboxylic acid were stirred at 140° C. for 4 hours in 166 ml of anhydrous dimethylformamide (DMF). 5.38 Parts of ammonium thiocyanate was added, and the mixture was stirred for additional 4 hours. After completion of the reaction, the mixture was allowed to cool to room temperature, and to stand for 36 hours. Afterward, the reaction solution was filtered, and the filtrate was poured into 830 parts of water, and the precipitated crystals were filtered off. The resultant crystals were washed twice with 2 parts of water, and then dried at 70° C. for 14 hours to obtain 2.78 parts of the compound (metal complex dye) of compound number (46) as a black brown crystal.

Measured values from absorption analysis of compound number (46) were as follows.

Measurement of absorption

Maximum absorption wavelength (λmax)=387 nm, molecular extinction coefficient (ε)=40563 (solvent: dimethylsulfoxide:ethanol=1:9 mixed solution)

This compound has the maximum absorption wavelength also at 530 nm, and the molecular extinction coefficient (ε) at 530 nm was 17750.

Example 4 and Example 5

A titanium oxide dispersion, PASOL HPW-18NR (from Shokubai Kasei Kogyo K.K.) was made into a paste, and was applied onto a transparent conductive glass electrode to form a titanium oxide film. To a semiconductor thin film obtained by sintering the titanium oxide film at 450° C. for 30 minutes, about 1 cc of a 0.04 M titanium tetrachloride aqueous solution was added dropwise followed by standing at 60° C. for 30 minutes and water washing, and then again calcination at 450° C. for 30 minutes to obtain a porous substrate having a titanium tetrachloride-treated semiconductor thin film (film thickness: 7 μm, measured by a surface roughness/shape measuring instrument Surfcom 570A from Tokyo Seimitu Co., Ltd.).

The metal complex dyes of compound number (6) obtained in Example 1 and of compound number (46) obtained in Example 3 were separately dissolved in a mixed solvent of tert-butanol:acetonitrile (1:1) so as to be 3.0×10$^{-4}$ M, and chenodeoxycholic acid was added so as to be 10 mM for compound number (6), and ursodeoxycholic acid was added so as to be 10 mM for compound number (46), respectively. To these solutions, the porous substrates obtained by the foregoing method were immersed at room temperature (20° C.) for 12 hours to make the respective substrates carry respective dyes, and then washed with the mixed solvent followed by drying to obtain photoelectric conversion devices of the present invention comprising a thin film of dye-sensitized semiconductor fine particles.

The solar cells of the present invention were obtained respectively by fixing oppositely the thin films of semiconductor fine particles of the photoelectric conversion devices of the present invention thus obtained, and a sputtered surface of conductive glass sputtered with platinum with a void space of 20 micrometer therebetween, and filling the void space by pouring a solution containing an electrolyte. As the electrolyte, a 3-methoxypropionitrile solution of (1,2-dimethyl-3-propylimidazolium iodide 0.6 M)+(LiI 0.1M)+(I$_2$ 0.1 M)+(tert-butylpyridine 0.5 M) was used.

The size of the efficient part of a cell to be measured was 0.25 cm$^2$. The light source was 100 mW/cm$^2$ through an AM (air mass) 1.5 filter. The short circuit current, the open circuit voltage, the conversion efficiency were measured by using solar simulator WXS-155S-10 AM1.5G (from Wacom Electric Co., Ltd.).

TABLE 4

| | Compound Number | Open circuit voltage (V) | Short circuit current (mA/cm$^2$) | Conversion efficiency |
|---|---|---|---|---|
| Example 4 | (6) | 0.71 | 13.63 | 6.17 |
| Example 5 | (46) | 0.68 | 14.90 | 6.14 |

In viewing the results of Table 4, it was confirmed that an excellent photoelectric conversion efficiency was obtained from the compounds of compound numbers (6) and (46), and even when the film thickness of titanium dioxide was thin, a sufficiently high conversion efficiency can be obtained.

The metal complex dye of the present invention is highly soluble in an organic solvent during a purification process or when being adsorbed on a titanium dioxide electrode, and therefore also has these excellent workability.

Industrial Applicability

By using a metal complex dye having a specific structure of the present invention or a salt thereof as a sensitized dye for a dye-sensitized photoelectric conversion device, even when the film of oxide semiconductor fine particles which carry a dye is thin, a photoelectric conversion device and a solar cell having a high conversion efficiency and high stability can be obtained.

The invention claimed is:

1. A photoelectric conversion device in which a metal complex dye represented by following Formula (1) or a salt thereof is carried on a thin film of oxide semiconductor fine particles disposed on a substrate:

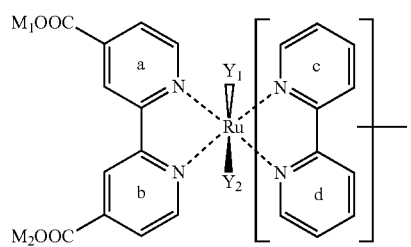

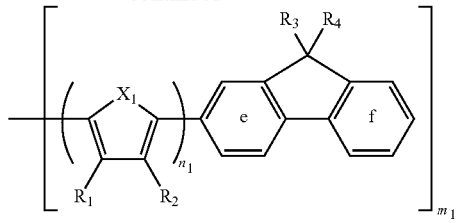

wherein, $m_1$ represents an integer of 1 to 2, $n_1$ represents an integer of 1 to 3; $X_1$ represents an oxygen atom or a sulfur atom; $Y_1$ and $Y_2$ each independently represent a thiocyanate group (—SCN) or an isothiocyanate group (—NCS); $M_1$ and $M_2$ represent a hydrogen atom; $R_1$ and $R_2$ represent a hydrogen atom; $R_3$ and $R_4$ each independently represent a straight alkyl group of 1 to 6 carbon atoms; with the proviso that when $m_1$ is 2 and $R_3$ and $R_4$ each exist in a plural number, then each $R_3$ and $R_4$ may be the same or different from each other.

2. The photoelectric conversion device according to claim 1, wherein $X_1$ in Formula (1) is a sulfur atom.

3. The photoelectric conversion device according to claim 2, wherein $n_1$ in Formula (1) is 1.

4. The photoelectric conversion device according to claim 3, wherein $Y_1$ and $Y_2$ in Formula (1) are each an isothiocyanate group (—NCS).

5. The photoelectric conversion device according to claim 4, wherein $R_3$ and $R_4$ in Formula (1) are each independently a straight alkyl group of 3 to 5 carbon atoms.

6. The photoelectric conversion device according to claim 5, wherein $R_3$ and $R_4$ in Formula (1) are each an n-butyl group.

7. The photoelectric conversion device according to claim 6, wherein $m_1$ in Formula (1) is 2.

8. The photoelectric conversion device according to claim 6, wherein $m_1$ in Formula (1) is 1.

9. The photoelectric conversion device of claim 1, further comprising a methine dye and/or a metal complex dye having a structure other than the Formula (1).

10. The photoelectric conversion device according to claim 1, wherein the thin film contains titanium dioxide, zinc oxide or tin oxide.

11. The photoelectric conversion device according to claim 1, wherein a metal complex dye or a salt thereof is carried under the presence of a chlathrate compound.

12. A solar cell using a photoelectric conversion device according to any one of claims 1 to 11.

13. A metal complex dye represented by Formula (1) or a salt thereof:

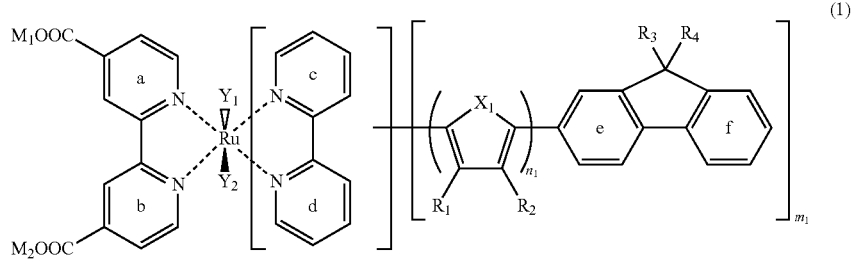

wherein, $m_1$ represents an integer of 1 to 2, $n_1$ represents an integer of 1 to 3; $X_1$ represents an oxygen atom or a sulfur atom; $Y_1$ and $Y_2$ each independently represent a thiocyanate group (—SCN) or an isothiocyanate group (—NCS); $M_1$ and $M_2$ represent a hydrogen atom; $R_1$ and $R_2$ represent a hydrogen atom; $R_3$ and $R_4$ each independently represent a straight alkyl group of 1 to 6 carbon atoms; with the proviso that when $m_1$ is 2 and $R_3$ and $R_4$ each exist in a plural number, then each $R_3$ and $R_4$ may be the same or different from each other.

14. A photoelectric conversion device in which a metal complex dye represented by following Formula (1) or a salt thereof is carried on a thin film of oxide semiconductor fine particles disposed on a substrate:

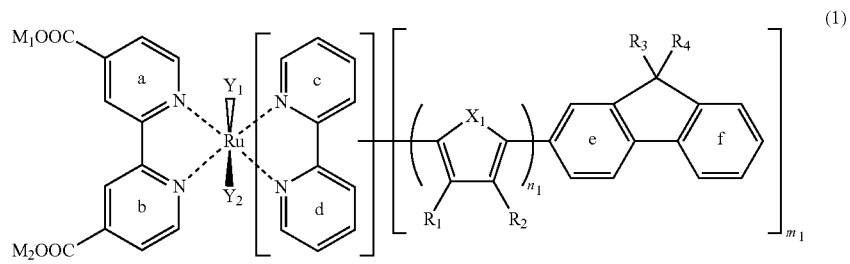

wherein, $m_1$ represents an integer of 1 to 2, $n_1$ represents an integer of 1 to 3; $X_1$ represents an oxygen atom, a sulfur atom, a selenium atom or $=NR_5$ wherein $R_5$ represents a hydrogen atom or an aliphatic hydrocarbon residue which may have a substituent; $Y_1$ and $Y_2$ each independently represent a thiocyanate group (—SCN), a halogen atom or an isothiocyanate group (—NCS); and $Y_1$ and $Y_2$ may be combined together to form one ligand; $M_1$ and $M_2$ each independently represent a hydrogen atom or an ammonium ion; $R_1$ and $R_2$ each independently represent a hydrogen atom, an aliphatic hydrocarbon residue which may have a substituent or an alkoxyl group which may have a substituent; and when $n_1$ is 2 or more, or $m_1$ is 2 and $R_1$ and $R_2$ each exist in a plural number, then each $R_1$ and $R_2$ may be the same or different from each other; and a plural of $R_1$ and/or $R_2$ may form a ring, and further may have a substituent on this ring; $R_3$ and $R_4$ each independently represent a hydrogen atom, an aliphatic hydrocarbon residue which may have a substituent or an aromatic hydrocarbon residue which may have a substituent; when $m_1$ is 2 and $R_3$ and $R_4$ each exist in a plural number, then each $R_3$ and $R_4$ may be the same or different from each other; and $R_3$ and $R_4$ may be combined each other to form a ring which may have a substituent; an aromatic ring a, an aromatic ring b, an aromatic ring c, an aromatic ring d and an aromatic ring e each may have 1 to 3 substituents; and an aromatic ring f may have 1 to 4 substituents.

* * * * *